United States Patent [19]

Calnek et al.

[11] Patent Number: 5,700,815
[45] Date of Patent: Dec. 23, 1997

[54] METHODS OF INCREASING THROMBOMODULIN EXPRESSION

[75] Inventors: David S. Calnek; Brian W. Grinnell, both of Indianapolis, Ind.

[73] Assignee: Eli Lilly and Company, Indianapolis, Ind.

[21] Appl. No.: 517,517

[22] Filed: Aug. 21, 1995

Related U.S. Application Data

[63] Continuation of Ser. No. 170,944, Dec. 21, 1993, Pat. No. 5,476,862.
[51] Int. Cl.⁶ .......................... A61K 31/445; A61K 31/40
[52] U.S. Cl. ...................... 514/324; 514/422; 514/443
[58] Field of Search ................................. 514/324, 422, 514/443

[56] References Cited

U.S. PATENT DOCUMENTS

| | | |
|---|---|---|
| 4,133,814 | 1/1979 | Jones et al. . |
| 4,380,635 | 4/1983 | Peters . |
| 4,418,068 | 11/1983 | Jones . |
| 5,075,321 | 12/1991 | Schreiber . |

FOREIGN PATENT DOCUMENTS

| | | |
|---|---|---|
| WO93/10113 | 5/1993 | Japan . |
| WO93/1074 | 6/1993 | WIPO . |

OTHER PUBLICATIONS

Abstract of Steroids, Dec. 1993, 58 (12), pp. 605–610. Radwanka.
Draper et al., "Effects of Raloxifene (LY139481 HCl) on Biochemical Markers of Bone and Lipid Metabolism i Healthy Postmenopausal Women", Hong Kong, Fourth Int'l Symp. on Osteoporosis, Mar. 29, 1993.
Bryant et al., "Protection from Bone Loss and Lowering of Serum Cholesterol in the Absence of Uterine Stimulation in Ovariectomized Rats", Am. Soc. Bone & Min. Res., Tampa, Sep. 18–22, 1993.
Bryant et al., "Raloxifene is a Tissue Specific Estrogen Agonist", Am. Soc. Bone & Min. Res., Tampa, Sep. 18–22, 1993.
Frolick et al., "In Vivo and In Vitro Metabolism of Raloxifene", Am. Soc. Bone & Min. Res., Tampa, Sep. 18–22, 1993.
Glasebrook et al., "Multiple Binding Sites for the Anti–estrogen Raloxifene", Am Soc. Bone & Min. Res., Tampa, Sep. 18–22, 1993.
Hock et al., "Combination of Raloxifene and Human Parathyoid Hormone 1–34; Increased Femur Bone Mass in Young Ovariectomized (OVX) Rats", Am. Soc. Bone & Min. Res., Tampa, Sep. 18–22, 1993.
Sato et al., "DEXA Analysis of Raloxifene Effects on the Bones From Ovariectomized Rats", Am. Soc. for Bone and Min. Res., Tampa, Sep. 18–22, 1993.
Yang et al., "Raloxifene an Anti–Estrogen, Simulates the Effects of Estrogen in Inhibiting Bone Resorption Through Regulating TGFB–3 Expression in Bone;" .Am Soc. for Bone and Min. Res., Tampa, Sep. 18–22, 1993.

Black et al., "Distinct, Structure–Related Profiles of Estrogenic and Anti–Estrogenic Activity in the Tamoxifen and LY117018 Series;" The Endocrine Society, Abstract 1982.
Black et al., "Uterine Bioassay of Tamoxifen, Trioxifene, and New Estrogen Antagonist (LY117018) in Rats and Mice," Life Sciences, 26:1980, 1453–1458.
Black et al., "Differential Interaction of Antiestrogens with Cytosol Estrogen Receptors," Molecular and Cellular Endocrinology, 22:1981, 95–103.

(List continued on next page.)

*Primary Examiner*—Zohreh Fay
*Attorney, Agent, or Firm*—James J. Sales

[57] ABSTRACT

A method of increasing thrombomodulin expression comprising administering to a human in need of treatment an effective amount of a compound having the formula

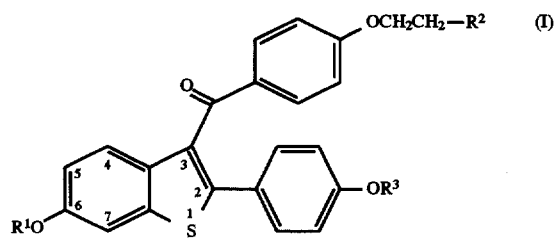

wherein
$R^1$ and $R^3$ are independently hydrogen, wherein
Ar is optionally substituted phenyl;
$R^2$ is selected from the group consisting of pyrrolidino, hexamethyleneamino, and piperidino; or a pharmaceutically acceptable salt of solvate thereof.
wherein
$R^1$ and $R^3$ are independently hydrogen, wherein
Ar is optionally substituted phenyl;
$R^2$ is selected from the group consisting of pyrrolidino, hexamethyleneimino, and piperidino; and pharmaceutically acceptable salts and solvates thereof.

Also encompassed by the invention is a method of inhibiting a thrombotic disorder or event which includes administering to a human in need thereof an effective amount of a compound of formula 1.

Also encompassed by the invention is a method of increasing Protein C activation rate which includes the administration of a compound of formula 1.

5 Claims, No Drawings

OTHER PUBLICATIONS

Black et al., "Evidence for Biological Action of the Antiestrogens LY117018 and Tamoxifen by Different Mechanisms," Endocrinology 109;1981, 987–989.

Black, L.J. "Biological Actions and Binding Properites of a New Estrogen Antagonists LY117018," In: Homone Antagosist, 129–82, 1982 (M.K. Agarwal ed.) Walter de Gruyter and Co., Berlin New York.

Black et al., LY156758: A Unique Antiestrogen Displaying High Affinity for Estrogen Receptors, Negligible Estrogenic Activity and Near–Total Estrogen Antagonism in Vivo. Presented at the Fifth Annual San Antonio Breast Cancer Symposium, San Antonio, Texas, Nov. 5–6, 1982.

Black et al., The Antiestrogenic Action of LY139481: Species Uniformity Duration of Action and Kinetics of 3H–LY139481 Distribution In Vivo. Sixty–fifth Annual Meeting of the Endocrine Society, San Antonio, Texas, Jun. 8–10, 1983, abs. 93.

Black et al., Antagonism of Estrogen Action with a New benzothiophene Derived Antiestrogen, Life Sciences, 32:1983. 1031–1036.

Black et al., The Relationship of the Antiestrogenic Efficacy of LY156758 to its Pharmacokinetics and Metabolism Following Oral Administration to Adult Ovariectomized Rats, Seventh International Congress of Endocrinology, Quebec City, Canada, Jul. 1–7, 1984, abs. 323.

Black et al., Synthesis and Antiestrogenic Activity of [3,4–Dihydro–2(4–methoxyphenyl)–1–napthalenyl] [4–[2–pyrrolidinyl) ethoxyl]–phenyl] methanone, methanesulfonic acid salt, Journal of Medicinal Chemistry 22;1979, 962–966.

Black et al., Antiestrogens 2. Structure Activity Studies in a Series of 3–Aroyl–2–arylbenzo[b]thiophene Derivatives Leading to [6–Hydroxy–2–(4–hydroxyphenyl)benzo[b]thien–3–yl][4–([2–(1–piperidinyl)ethoxy]–phenyl]methanone Hydrochloride (LY156758), a Remarkably Effective Estrogen Antagonist with Only Minimal Intrinsic Estrogenicity, J. Med. Chem. 27(8), 1984, 1057–1066.

METHODS OF INCREASING THROMBOMODULIN EXPRESSION

This application is a continuation, of application Ser. No. 08/170,944 filed Dec. 21, 1993, now U.S. Pat. No. 5,476,862.

BACKGROUND OF THE INVENTION

The process of blood coagulation, thrombosis, is triggered by a complex proteolytic cascade leading to the formation of thrombin. Thrombin proteolytically removes activation peptides from the Aα and Bβ-chains of fibrinogen, which is soluble in blood plasma, initiating insoluble fibrin formation.

Anti-coagulation is currently achieved by the administration of heparins and coumarins. Parenteral pharmacological control of coagulation and thrombosis is based on inhibition of thrombin through the use of heparins. Heparins act indirectly on thrombin by accelerating the inhibitory effect of endogenous antithrombin III (the main physiological inhibitor of thrombin). Because antithrombin III levels vary in plasma and because surface-bound thrombin seems resistant to this indirect mechanism, heparins can be an ineffective treatment. Because certain coagulation assays are believed to be associated with efficacy and safety, heparin levels are typically monitored with coagulation assays (particularly the activated partial thromboplastin time (APTT) assay). Coumarins impede the generation of thrombin by blocking the posttranslational gamma-carboxylation in the synthesis of prothrombin and other proteins of this type. Because of their mechanism of action, the effect of coumarins can only develop slowly, 6–24 hours after administration. Further, they are not selective anticoagulants. Coumarins also require monitoring with coagulation assays (particularly the prothrombin time assay).

To better understand the invention, the following brief description of the coagulation enzyme system is provided. The coagulation system, sometimes referred to as the "cascade", is best looked at as a chain reaction involving the sequential activation of zymogens into active serine proteases which eventually lead to the production of the enzyme, thrombin. Thrombin, through limited proteolysis, converts plasma fibrinogen into the insoluble gel, fibrin. Two key events in the coagulation cascade are the conversion of clotting Factor X to Xa by clotting factor IXa and the conversion of prothrombin into thrombin by clotting factor Xa.

Both of these reactions occur on cell surfaces, most notably the platelet endothelial cell surfaces, and both reactions require cofactors. The major cofactors, factors V and VIII, circulate as relatively inactive precursors, but when the first few molecules of thrombin are formed, thrombin activates, by limited proteolysis, the cofactors. The activated cofactors, Va and VIIIa, accelerate, by about three orders of magnitude, both the conversion of prothrombin into thrombin and the conversion of factor X to factor Xa.

Activated protein C overwhelmingly prefers two plasma protein substrates which it hydrolyzes and irreversibly destroys. These plasma protein substrates are the activated forms of clotting cofactors V and VIII (cofactors Va and VIIIa, respectively). Activated protein C only minimally degrades the inactive precursors, clotting factors V and VIII. In dogs, activated protein C has been shown to sharply increase circulating levels of the major physiological fibrinolytic enzyme, tissue plasminogen activator.

The activation of protein C, however, involves thrombin, the final serine protease in the coagulation cascade, and an endothelial cell membrane-associated glycoprotein, thrombomodulin. Thrombomodulin forms a tight 1:1 stoichiometric complex with thrombin. Thrombomodulin, when complexed with thrombin, modifies substantially the functional properties of thrombin. Thrombin, in the coagulation pathway, normally clots fibrinogen, activates platelets, and converts clotting cofactors V and VIII to their activated forms, Va and VIIIa. Thrombin, alone, acts to activate Protein C, but only very slowly and inefficiently. In contrast, thrombin, when in the a 1:1 complex with thrombomodulin, fails to clot fibrinogen, does not activate platelets, and does not convert clotting factors V and VIII to their activated forms. The thrombin:thrombomodulin complex promotes the activation of protein C with the rate constant of protein C activation being as great as 20,000-fold higher for the thrombin:thrombomodulin complex than the rate constant for thrombin alone.

Activated protein C, therefore, is an antithrombotic agent with a wider therapeutic index than other anticoagulants, such as heparin and the oral hydroxycoumarin-type anticoagulants, such as warfarin. Neither protein C nor activated protein C is effective until thrombin is generated at some local site. Activated protein C is virtually ineffective without thrombin, because thrombin is needed to convert clotting factors V to Va and VIII to VIIIa. As noted, the activated forms of these two cofactors are the preferred substrate for activated protein C. The protein C zymogen, when infused into patients, will remain inactive until thrombin is generated. Without the thrombomodulin:thrombin complex, the protein C zymogen is converted into activated Protein C at a very slow rate.

The present invention is directed to the discovery that the compounds of the present invention, as defined below, increase thrombomodulin expressions and have oral bioavailability.

SUMMARY OF THE INVENTION

This invention provides methods of increasing thrombomodulin expression comprising administering to a human in need thereof an effective amount of a compound of formula I

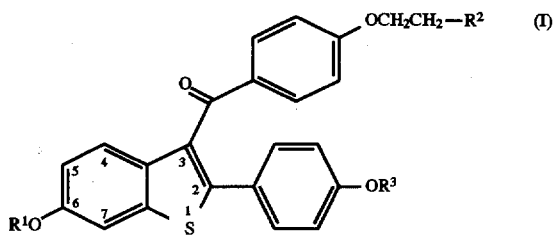

wherein $R^1$ and $R^3$ are independently hydrogen,

wherein

Ar is optionally substituted phenyl;

$R^2$ is selected from the group consisting of pyrrolidino, hexamethyleneimino, and piperidino; and pharmaceutically acceptable salts and solvates thereof.

Also encompassed by the invention is a method of inhibiting a thrombotic disorder or event which includes administering to a human in need thereof an effective amount of a compound of formula 1.

Also encompassed by the invention is a method of increasing Protein C activation rate which includes the administration of a compound of formula 1.

DETAILED DESCRIPTION OF THE INVENTION

The current invention concerns the discovery that a select group of 2-phenyl-3-aroylbenzothiophenes (benzothiophenes), those of formula I, are useful for increasing thrombomodulin expression. The methods of use provided by this invention are practiced by administering to a human or mammal in need thereof a dose of a compound of formula I or a pharmaceutically acceptable salt or solvate thereof, that is effective to increase thrombomodulin expression. The present method includes both medical therapeutic and/or prophylactic treatment, as appropriate.

Inhibit is defined to include its generally accepted meaning which includes retarding, preventing, restraining, slowing or reversing.

Raloxifene, a compound of this invention is the hydrochloride salt of a compound of formula 1, wherein $R^1$ and $R^3$ are hydrogen and $R^2$ is 1-piperidinyl.

Generally, the compound is formulated with common excipients, diluents or carriers, and compressed into tablets, or formulated as elixirs or solutions for convenient oral administration, or administered by the intramuscular or intravenous routes. The compounds can be administered transdermally, and may be formulated as sustained release dosage forms and the like.

The compounds used in the methods of the current invention can be made according to established procedures, such as those detailed in U.S. Pat. Nos. 4,133,814, 4,418,068, and 4,380,635 all of which are incorporated by reference herein. In general, the process starts with a benzo[b]thiophene having a 6-hydroxyl group and a 2-(4-hydroxyphenyl) group. The starting compound is protected, alkylated or acylated, and deprotected to form the formula I compounds. Examples of the preparation of such compounds are provided in the U.S. patents discussed above. Optionally substituted phenyl includes phenyl and phenyl substituted once or twice with $C_1$-$C_6$ alkyl, $C_1$-$C_4$ alkoxy, hydroxy, nitro, chloro, fluoro, or tri(chloro or fluoro)methyl.

The compounds used in the methods of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include ammonium hydroxide, potassium carbonate, methylamine, diethylamine, ethylene diamine and cyclohexylamine.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, the compounds can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonire; and lubricants such as talc, calcium and magnesium stearate, and solid polyethyl glycols.

The compounds can also be formulated as elixirs or solutions for convenient oral administration or as solutions appropriate for parenteral administration, for instance by intramuscular, subcutaneous or intravenous routes. Additionally, the compounds are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

The particular dosage of a compound of formula I required to increase thrombomodulin expression, inhibit a thrombotic disorder or event, or increase the Protein C activation rate, according to this invention, will depend upon the severity and nature of the condition, the route of administration, and related factors that will be decided by the attending physician. Generally, accepted and effective daily doses will be from about 0.1 to about 1000 mg/day, and more typically from about 50 to about 200 mg/day. Such dosages will be administered to a subject in need of treatment from once to about three times each day, or more often as needed to effectively increase thrombomodulin expression, increase Protein C activation, or inhibit thrombotic disorders.

It is usually preferred to administer a compound of formula I in the form of an acid addition salt, as is customary in the administration of pharmaceuticals bearing a basic group, such as the piperidino ring. It is also advantageous to administer such a compound by the oral route. For such purposes the following oral dosage forms are available.

FORMULATIONS

In the formulations which follow, "active ingredient" means a compound of formula I.

Formulation 1: Gelatin Capsules

Hard gelatin capsules are prepared using the following:

| Ingredient | Quantity (mg/capsule) |
| --- | --- |
| Active ingredient | 0.1–1000 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules.

Examples of specific capsule formulations of raloxifene that have been made include those shown below:

Formulation 2: Raloxifene capsule

| Ingredient | Quantity (mg/capsule) |
| --- | --- |
| Raloxifene | 1 |
| Starch, NF | 112 |
| Starch flowable powder | 225.3 |
| Silicone fluid 350 centistokes | 1.7 |

Formulation 3: Raloxifene capsule

| Ingredient | Quantity (mg/capsule) |
| --- | --- |
| Raloxifene | 5 |
| Starch, NF | 108 |
| Starch flowable powder | 225.3 |
| Silicone fluid 350 centistokes | 1.7 |

Formulation 4: Raloxifene capsule

| Ingredient | Quantity (mg/capsule) |
| --- | --- |
| Raloxifene | 10 |
| Starch, NF | 103 |
| Starch flowable powder | 225.3 |
| Silicone fluid 350 centistokes | 1.7 |

Formulation 5: Raloxifene capsule

| Ingredient | Quantity (mg/capsule) |
| --- | --- |
| Raloxifene | 50 |
| Starch, NF | 150 |
| Starch flowable powder | 397 |
| Silicone fluid 350 centistokes | 3.0 |

The specific formulations above may be changed in compliance with the reasonable variations provided.

A tablet formulation is prepared using the ingredients below:

Formulation 6: Tablets

| Ingredient | Quantity (mg/tablet) |
| --- | --- |
| Active ingredient | 0.1–1000 |
| Cellulose, microcrystalline | 0–650 |
| Silicon dioxide, fumed | 0–650 |
| Stearate acid | 0–15 |

The components are blended and compressed to form tablets.

Alternatively, tablets each containing 0.1–1000 mg of active ingredient are made up as follows:

Formulation 7: Tablets

| Ingredient | Quantity (mg/tablet) |
| --- | --- |
| Active ingredient | 0.1–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 mL dose are made as follows:

Formulation 8: Suspensions

| Ingredient | Quantity (mg/5 ml) |
| --- | --- |
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

In a further embodiment the invention relates to treatment, in a human or animal, of conditions where inhibition of a thrombotic disorder is required. Thrombotic disorders or events, or thromboembolic diseases, include a wide variety of acquired disease states involving intravascular coagulation, including deep vein thrombosis, pulmonary embolism, myocardial ischemia, myocardial infarction, cerebral thrombosis, general states, local hypercoaguable states and generalized tissue injury as it relates to the inflammatory process, microvascular arterial thrombosis, peripheral arterial thrombosis, emboli originating from the heart or peripheral arteries, acute myocardial infarction, thrombotic strokes, and disseminated intravascular coagulation. Disseminated intravascular coagulation occurs as a complication to numerous disease states including major trauma, major surgery, heat stroke, septicemia, acute and chronic liver disease, malignancies including solid tumors, leukemias and lymphomas, a wide variety of bacterial, fungal, parasitic and viral infections, obstetrical complications, hemolytic processes, cardiogenic shock, circulatory collapse from any cause, severe progressive strokes, snake bites, collagen vascular disorders, purpura fulminans, acute pancreatitis, allergic vasculitis, polycythemia vera, thrombocythemia, and ulcerative colitis among others. Although not yet discovered, congenital deficiencies in the expression of the thrombomodulin may be demonstrated in patients with thromboembolic problems. Acute episodes in such patients will be amenable to treatment with the compounds of Formula 1.

Compounds of formula 1 are also believed to be useful in the treatment of thrombotic strokes. Thrombomodulin levels are low in vessels in the brain, thus upregulation will be important in thrombotic stroke. Today, strokes are not usually treated with conventional anticoagulants. Treatment of strokes with either heparin or oral anti-coagulants, although occasionally beneficial, carries a high risk for bleeding into the infarcted brain area, thereby aggravating the neurological deficit accompanying the stroke.

Further, the present compounds are believed to be useful in the treatment of acute myocardial infarction because there is evidence that the major mechanism of action of thrombomodulin and derivatives provided, that is, the activation of the protein C anticoagulant pathway, constitutes a highly effective means of achieving antithrombotic effects on the arterial side of the circulation, as well as reducing reperfusion injury. In current trials with thrombolytic agents in acute myocardial infarction and from animal experiments, it would appear that heparin, as adjunct therapy, is relatively ineffective, as an antithrombotic agent on the arterial side of the circulation.

Also, the present compounds are believed to be useful in the treatment of disseminated intravascular coagulation ("DIC"). There is experimental evidence that inflammatory mediators such as IL-1, TNF, and LPS endotoxin sharply down regulate the expression of thrombomodulin on endothelial cells leading in turn to defective activation of the protein C anticoagulant pathways. Heparin and the oral anticoagulants have been given to patients with disseminated intravascular coagulation in extensive clinical trials, but the results of these trials have been disappointing. Characteristically, patient with disseminated intravascular coagulation have widespread thrombi involving the microcirculation with concomitant and often severe bleeding problems, which result from "consumption" of essential clotting factors, which have been first activated and then inactivated during the formation of widespread microcirculatory fibrin thrombi.

Because thrombomodulin is down regulated by a variety of inflammatory mediators, a preferred use of the compounds is in correcting inflammatory conditions associated with microvascular thrombosis. Broadly this would include any condition marked by dysfunctional vascular endothelium as occurs in sepsis, injuries involving major tissue damage and trauma, systemic inflammatory response syndrome, sepsis syndrome, septic shock, and multiple organ dysfunction syndrome, including DIC.

Evidence exists that conventional anticoagulant drugs, particularly warfarin, are useful in the treatment of invasive malignant tumors. Many tumor cells produce substances which trigger the activation of the coagulation system resulting in local fibrin deposits. These fibrin deposits function as "nests" in which cancer cells can divide to form metastatic lesions. In one clinical study, it was shown that patients receiving warfarin in addition to cancer chemotherapy for treatment of small cell carcinoma of the lung live longer and have less extensive metastatic lesions than patients receiving chemotherapy alone. However, the cancer chemotherapy utilized in this study was less intensive than that considered optimal in clinical oncology today. The more intensive forms of cancer chemotherapy almost always produce a sharp decline in the platelet count, and thrombocytopenia combined with warfarin therapy puts the patient in an unacceptably high risk for serious bleeding complications.

The compounds are expected to have utility in other diseases where blood coagulation could be a fundamental contributing process or source of secondary pathology, such as cancer, including matastisis, inflammatory diseases, including arthritis, and diabetes. The anti-coagulant compound is administered orally, parenterally e.g. by intravenous infusion (iv), intramuscular injection (im) or subcutaneously (sc).

The method of this invention also is practiced in conjunction with a clot lysing agent e.g. tissue plasminogen activator (tPA), modified tPA, streptokinase or urokinase to reduce reperfusion injury. In cases when clot formation has occurred and an artery or vein is blocked, either partially or totally, a clot lysing agent is usually employed. A compound of the invention can be administered prior to or along with the lysing agent or subsequent to its use alone or along with the lysing agent and preferably further is administered along with aspirin to prevent the reoccurrence of clot formation.

The method of this invention is also practiced in conjunction with a platelet glycoprotein IIb–IIIa receptor antagonist, that inhibits platelet aggregation. A compound of the invention can be administered prior to or along with the IIb–IIIa receptor antagonist or subsequent to its use to prevent the occurrence or reoccurrence of clot formation.

The method of this invention is also practiced in conjunction with aspirin. A compound of the invention can be administered prior to or along with aspirin or subsequent to its use to prevent the occurrence or reoccurrence of clot formation. As stated above, preferably a compound of the present invention is administered in conjunction with a clot lysing agent and aspirin.

ASSAYS

Assay 1

To further understand the action(s) of the compounds of formula 1, intimal smooth muscle cells and its role in enhancing anticoagulation of blood, it is necessary to investigate changes in thrombomodulin (TM) activity on the surface of these cell types. The compounds of formula 1 may also be used to reverse/correct any effects of mediators that tend to down regulate TM activity on the surface of these cells.

Approximately 40,000–80,000 early passaged endothelial (arterial, venous, or microvascular), or intimal smooth muscle cells are seeded and grown to confluency in 24-well cell culture plates. The cell monolayer is subsequently washed 2–3 times with either Hank's buffered saline solution (HBSS), or serum-free medium (SFM). For a period of 24 hours, varying concentrations of a compound of formula 1 (ranging from micromolar to subpicomolar) are added to the cells in triplicate. The cells residing in negative control wells are maintained on serum-free medium with an amount of vehicle equivalent among all wells.

The existing method to measure cell surface TM activity is performed by using a two-phase amidolytic assay. During the first phase of the assay, following rinsing of the cells with HBSS or SFM, 0.4ml SFM containing human protein C (final concentration 11.2 ug/ml) and human alpha-thrombin (final concentration 0.1 NIHU/ml) are added to the monolayer and incubated at 37° C. and 5% $CO_2$. At 15, 30, and 45 minute time points, 100 ul of medium is removed from each well and added to 50 ul of excess hirudin (20 antithrombin U/ml) in microtiter wells for 5 minutes at 37° C. in order to arrest further thrombin activity. In the absence of cells, SFM plus protein C and alpha-thrombin, as described above, is used as a negative control and treated similarly.

In the second phase of the assay, 50 ul of 3 mM 2366, a chromogenic substrate of protein C, is added to the conditioned media/hirudin mixture and the $OD_{405}$ is measured by an automatic plate reader to monitor the kinetics of TM activity over a 4 minute period. Upon completion of this kinetic assay, measurement of total protein is performed using the BCA method. The final TM activity is expressed as % increase. Compound A is a compound of formula 1 wherein $R^1$ and $R^3$ are hydrogen, and $R^2$ is 1-pyrrolidino.

| Compound A conc. (μM) | TM Activity (% increase) |
|---|---|
| $1 \times 10^{-4}$ | 14 |
| $1 \times 10^{-2}$ | 15 |
| $1 \times 10^{-1}$ | 15 |
| 1.00 | 17 |
| 10.00 | 17 |

Assay 2

The baboon model of *E. Coli*-induced sepsis as described in U.S. Pat. No. 5,009,889 (incorporated herein by reference) is used to illustrate the compounds of formula 1 effects as antithrombotics and their ability to correct inflammation-induced endothelial dysfunction.

Utility of the compounds of the invention is illustrated by the positive impact on thrombomodulin expression, thrombotic disorder, or Protein C activation rate characteristics displayed by any of the above assays.

We claim:

1. A method of inhibiting a thrombotic disorder or event comprising administering to a human in need an effective amount of a compound of the formula

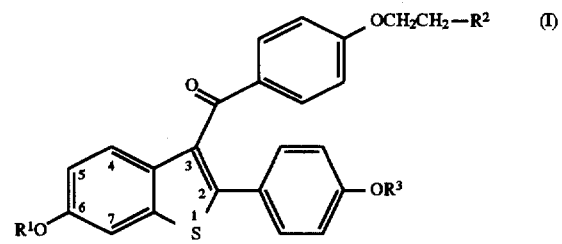

wherein $R^1$ and $R^3$ are independently hydrogen,

wherein

Ar is optionally substituted phenyl;

$R^2$ is selected from the group consisting of pyrrolidino, hexamethylenemino, and piperidino; or a pharmaceutically acceptable salt of solvate thereof.

2. The method of claim 1 wherein said compound is the hydrochloride salt thereof.

3. The method of claim 1 wherein said administration is prophylactic.

4. The method of claim 1 wherein said thrombotic disorder or event is an inflammatory condition associated with microvascular thrombosis.

5. The method of claim 1 wherein said compound is

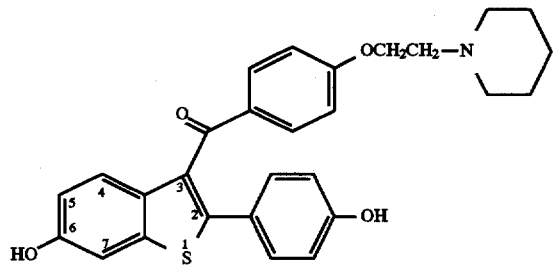

or its hydrochloride salt.

* * * * *